US005645824A

United States Patent [19]
Lim et al.

[11] Patent Number: 5,645,824
[45] Date of Patent: Jul. 8, 1997

[54] COLOR CHANGING REAGENT COMPOSITION FOR COATING ON NEEDLES USED IN MEDICAL APPLICATIONS

[76] Inventors: Min H. Lim, 502 Andrew St., Greenbrook, N.J. 08812; Michael G. Marinangleli, 244 E. 86 St. #23, New York, N.Y. 10028

[21] Appl. No.: 541,488

[22] Filed: Oct. 2, 1995

[51] Int. Cl.$^6$ .............................. D06P 5/00; C09B 67/00; G01N 33/00; A61M 5/00

[52] U.S. Cl. .................... 424/70.1; 252/408.1; 436/183; 604/111; 604/187; 424/422

[58] Field of Search ................................ 8/400, 401, 651; 252/408.1; 436/183; 604/111, 187; 424/7.1, 422

[56] References Cited

U.S. PATENT DOCUMENTS 3,627,469  12/1971  Cheng ........................... 8/400
4,942,132   7/1990  Lawrence ....................... 436/66

Primary Examiner—Thurman K. Page
Assistant Examiner—Kathryne E. Shelborne
Attorney, Agent, or Firm—MGM & Associates Michael Marinangelli

[57] ABSTRACT

A color changing reagent composition for coating onto syringe needles and other needle containing medical devices which upon contact with such bodily fluids as blood, mucous, saliva, and semen will cause the composition coated needle to change in color to signal a prior use and contamination with a possibly infected bodily fluid. The preferred composition is selected from the group consisting of guaiac acid, benzidine, Barfoeds solution, Benedicts solution, cresol, catechol, phenylenediamine, Haynes solution, phenol, leuco malachite green, leuco-crystal violet, peroxidase, pseudoperoxidase, orthotolodine, orthordianisidine, cumene hydroperoxide, tretramethylbenzedene and 2,2-azinodi-(3-ethylbenzyl)azoline sulfunic acid. After the coated needle comes in contact with a bodily fluid having a catalyst it will, upon oxidation, change from being in a colorless state to having a visually detectable color. The invention will reduce both the mistaken or even intentional re-use of used and possibly disease contaminated needles and provides a revolutionary means of minimizing the continued spread of such bodily fluid transfered diseases as AIDS and Hepatitis B.

3 Claims, No Drawings

COLOR CHANGING REAGENT COMPOSITION FOR COATING ON NEEDLES USED IN MEDICAL APPLICATIONS

FIELD OF THE INVENTION

The present invention relates to a color changing reagent composition for coating needles. More particularly, the invention is to a reagent composition for coating needles used in medical applications of all types that will give a visual forewarning after it has come in contact with another persons bodily fluid, a catalyst. The composition coated needle will change in color thus signaling that it has already been used and possibly contaminated with diseased bodily fluid. The present invention can be applied and used on any type of known needles for medical use by coating the needle portion with a leuco dye reagent. After the reagent comes in contact with bodily fluid, a hydroperoxide catalyst, the later oxidation of the needle upon removal from the body will cause the coated needle to change from colorless to a visually detectable blue, green or violet color.

DESCRIPTION OF THE PRIOR ART

There are presently known numerous types of needles used in medical applications, which although having various safety features for minimizing the spread of diseases, all lack the simple yet inventive, and never before conceived improvement that is claimed herein.

As is well-known, the repetitious use of needles used on medical syringes without proper sterilization is in a large part responsible for the tragic spread of diseases, such as AIDS and Hepatitis B, among others. This problem has resulted in the development and patenting of numerous disposable and single use medical devices such as needle syringes which are produced and made available to anyone requesting them. Unfortunately, these so-called "disposable" syringes are disposable in theory only and, in actual practice, are readily capable of re-use, as are conventional syringes. Moreover since sterilization of reusable syringes requires special equipment and is time consuming and expensive, the use of cheaper and expendible syringes has increased.

Numerous syringes designed for a single use are also known. A wide variety of such syringes have been patented. Although their claimed objective of minimizing the spread of diseases is desirable they are complex in structure and thus expensive for both the manufacturer and the end user. The risk of spreading disease is therefore not wholly eliminated by these prior known disposable syringes.

The present invention, therefore, fills a large void in the medical industry's attempt to find a safe and effective needle for use in syringes and other bodily fluid contacting medical devices. The color changing composition coated needle described herein will minimize both the mistaken or even intentional re-use of used needles by medical personnel, drug users and abusers, and therefore minimize the spread of many fatal diseases that are transferred through bodily fluid contact. By coating needles with the reduced leuco dye composition claimed herein, users of medical syringes and other bodily fluid contacting medical devices will be visibly forewarned that the needle they are about to use has already come in contact with another person's bodily fluid. As used herein the composition termed "leuco dye" is not intended to be limited to a particular chemical species or genus but is intended to encompass indicators that produce a detectable response, that is a color change that is visible to the naked eye when oxidized after coming in contact with bodily fluid.

Examples of leuco dyes which are effective coatings that upon contact with a bodily fluid catalyst will change colors when oxidized are guaiac acid, benzidine, Barfoeds solution, Benedicts solution, cresol, catechol, phenylenediamine, Haynes solution, phenol, leuco malachite green, leuco-crystal violet, peroxidase, pseudoperoxidase, orthotolodine, orthordianisidine, cumene hydroperoxide, tretramethylbenzedene and 2,2-azinodi-(3-ethylbenzyl)azoline sulfunic acid. Thus, although this application discloses, by way of example, a leuco dye composition for coating needles so that said coated needle turns blue, green or violet in color upon contact with bodily fluid, other compositions, some not yet syntesized or specifically claimed herein, resulting in a visible needle color change, can also be used and are thus part of the herein claimed concept of coating a needle to visibly warn that is has already been in contact with bodily fluid.

Worldwide patents on single use, self needle syringes are too numerous to list in full. Representative patented features on syringes, having needles include "graphic visualization" (see U.S. Pat. No. 5,242,405); "protective shields" (see U.S. Pat. No. 5,222,945); "self-destructing design" (see U.S. Pat. No. 5,201,709); "single use" (see U.S. Pat. Nos. 5,370,620, 5,344,405, 5,308,331, 5,308,328); "throw away" (see U.S. Pat. No. 5,334,156); "aspiring non-re-useable" (see U.S. Pat. No. 5,352,203); "retractable needle" (see U.S. Pat. No. 5,346,480); "self destruct double syringe" (see U.S. Pat. No. 5,149,323). Although each one of the above listed patents discloses improvements in the features of hypodermic syringes all could be further improved to attain their listed objective of minimizing the spread of diseases through bodily fluid contact, by coating the needles portion of the syringe with the color changing composition disclosed herein. There is a major drawback in the above listed and other known needles. The problem is that the user cannot readily determine whether the needle has already come in contact with another's bodily fluids. The problem is especially acute in the case of AIDS, or other harmful viral diseases such as hepatitis-B, and certain bacterial infections which although are microscopically small, still contain microbial etiologic agents of these often fatal diseases. There are literally billions of such disease spreading agents in even a microscopic droplet of bodily fluid such as blood, mucous, saliva, and semen. Consequently, many persons using medical devices containing needles, including those that are alledgedly single use, disposable syringes, may be unwittingly exposed to an infectious agent such as the AIDS virus because the user cannot visually detect that the needle has already come in contact with a possibly diseased microscopic amount of blood or other bodily fluid. Coating needles, used on syringes and other bodily fluid contacting medical devices having needles, with the composition disclosed herein, or derivatives and advances thereof, would save thousands, if not millions of lives throughout the world in a relatively inexpensive yet effective way.

No earlier prior art taken either singly or in combination, is seen to describe the present invention as described herein and claimed by us below. Although useful for their claimed objectives no prior patent discloses a composition for coating bodily fluid contacting needles used in syringes and other medical devices which will give off a visible warning that it has already been used and therefore possibly infected and diseased.

OBJECTS OF THE INVENTION

The overall object of the present invention is to provide a means for reducing both the intentional and mistaken re-use of contaminated hypodermic syringe needles or other needle containing medical devices used in the intravenous injection of medication and drugs or other hypodermic applications by way of a visually detectable color changing reagent composition.

Another object of the present invention is to provide a reagent composition which when coated on medical devices having needles will give a visually detectable warning to medical professionals, intravenous drug users and abusers that a particular needle has already been used intravenously and in contact with bodily fluid or other possibly contaminated bodily fluid.

A still further object of the present invention is to provide an additional safety feature in known needle containing medical devices of all types that are used by people through out the world.

Still a further object of the present invention is to improve the safety features of known syringes of all types by way of coating the needle portion of said syringe with a reagent composition selected from any number of reduced leuco dyes, that upon contact with a hydroperoxide catalyst, such a blood, will upon intravenous use and removal, display a visually detectable colored oxidized leuco dye.

Another object of the present invention is to provide a color changing reagent coated needle for medical devices which will minimize the spread of AIDS and other diseases that are transferred through the sharing of such devices having needles with infected bodily fluids.

A final object of the present invention is to provide a color changing composition for coating onto needles which is safe and effective yet affordable to all users.

Other objects, advantages and novel features of the invention will become readily apparent to those skilled in the art from the following detailed description and examples of a preferred embodiment of the novel composition for coating needles.

DETAILED DESCRIPTION OF THE COMPOSITION IN A PREFERRED EMBODIMENT

One preferred embodiment of the invention is a composition for use as a coating on a needle comprising a mixture of guaiac acid and ABTS. The complete reagent for coating the needle body can have, in addition to the mixture of guaiac and ABTS, a solvent, a hyperperoxide, and optionally, other additives such as hemoprotein solubilizing agents, stabilizers, vegetable peroxidase, inhibitors, iron chelators, accelerators and known buffers. Such additives may be combined into the needle coating composition in various quantities so as to result in various sought after color strength. For example, the chromogen mixture of guaiac and ABTS produces a color change that is visually more detectable in its color change that would occur if guaiac or ABTS were used individually. The weight ratio of guaiac to ABTS in the composition mixture is in the range of 1:6 to 6:1, but preferably a 1 to 1 weight ratio. When the chromogen mixture is formulated as a complete reagent with a peroxide or in a solvent for iron protoporphyrins, it is preferable to include a stabilizing amount of sodium sulfite or such similar antioxidant in the composition. Preferably, the sodium sulfite is added in amounts in excess of that which saturates the solution. The concentration of the composition in the solution will usually be in the range of 0.5 to 10% by weight. Dimethylsulfoxide (DMSO) is one preferred choice of a iron protoporphyrin solvent. Using dimethylsulfoxide as the solvent in the reagent composition is preferred because it is an excellent solvent for hemoproteins, including iron protoporphyrins; it converts heme and hemin dimers and aggregates into monomeric forms; and peroxidases that may be in bodily fluid, a hydroperoxide catalyst, and inhibits them from catalyzing the oxidation of the color indicator in the composition and producing a false positive color change result.

Another embodiment of the invention comprises coating the needle with a leuco dye and a hydroperoxide, preferably wherein the hydroperoxide or the hydroperoxide and the leuco dye are applied to the needle in solution in a solvent comprising at least 50% by volume of the solvent for iron protoporphyrins whereby the iron protoporphyrins in the specimens are dissolved. Another embodiment of the composition comprises a leuco dye and a hydroperoxide wherein the leuco dye comprises a mixture of guaiac and ABTS. Still another embodiment of the needle coating is a composition comprising a hydroperoxide or a hydroperoxide and a leuco dye in solution in a solvent for iron protoporphyrins selected from the group consisting of:

(a) pyridine;

(b) a mixture of ethanolamine and a co-solvent selected from the group consisting of methlethyl ketone, tetramethylene sulfone, outrolacton, glycerol, methanol, tetrahydrofurfuryyl alcohol, 2-methroxy ethanol, and tetramethyl urea;

(c) a mixture of 2-diethylaminehethlamine) and a co-solvent selected from the group consisting of methl ethyl ketone, acetonitrile, tetramethylene sulfone, butyrolactone, tetrahydrofurfuryl alcohol, 2-methoxy ethanol, and methanol;

(d) a mixture of diethanolamine and a co-solvent selected from the group consisting of methyl ethyl ketone, acetonitrile, tetramethylene sulfone, butyrolactone, and tetrahydrofurfuryl alcohol; and (e) 1-methyl-2-pyrrolidinone.

EXAMPLE 1

This example shows the chromatographic advantages of a multi-chromogen reagent composition relative to a single chromogen reagent composition. The following comparative reagents were used:

I) Reagent Composition I—2% guaiac and 5% cumene hydroperoxide in dimethylsulfoxide.

II) Reagent Composition II—multi-chromogen reagent (2% guaiac, 5% cumene hydroperoxide, and 25 mg/ml 2,2-azino-di-(3-ethylbenzyl)thiazoline sulfonic acid in dimethylsulfoxide over 100 mg solid sodium sulfite).

Two μl of a hemin suspension in water (1 mg/ml) were touched to a coated needle, one having varing volumes of Reagent Composition I or Reagent Composition II, and the appearance of the color blue noted in Table 1 below:

TABLE 1

| Reagent Volume | Reagent Comp. I | Reagent Comp. II |
| --- | --- | --- |
| 5 ul–15 ul | dispersed color spotted light blue | undispered, intense blue color |

EXAMPLE 2

This example shows enhanced color intensity and uniformity obtained using a multi-chromogen reagent. The following reagent compositions were used:

I) Reagent Composition I—2% guaiac and 5% cumene hydroperoxide in dimethylsulfoxide.

II) Reagent Composition II—2% guaiac and 5% cumene hydroperoxide and 25 mg/ml 2,2-azino-di-(3-ethylbenzyl) thiazoline sulfonic acid in dimethylsulfoxide over 100 mg solid sodium sulfite.

10 μl of Reagent Composition I or Reagent Composition II was coated onto a needle body. Two μl of a hemin solution (0.05 mg/ml) in dimethylsulfoxide was touched to the coated needle and the color appearance noted within 180 seconds as noted in Table 2 below:

TABLE 2

| | Reagent Comp. I | | Reagent Comp. II | |
|---|---|---|---|---|
| | Intensity | Appearance | Intensity | Appearance |
| 1) | +3 | light blue | +10 | intense blue |

The preferred reagent composition described and claimed in this application can be applied by known means to the needle body. Although seemingly simple to use and inexpensive to manufacture, there is no prior art which anticipates or makes obvious the present life saving reagent composition for coating needles used in all types of medical applications. This convenient and inexpensive composition for coating needles used in syringes and other medical devices will give off a visible warning that it has already been used and therefore possibly infected and diseased.

Since the invention is described with reference to various preferred embodiments, and since numerous modifications and changes may become readily apparent to those skilled in the art after reading this disclosure, it should be understood that we do not wish to limit the scope of our overall invention to the exact composition or particular color change described above and as claimed by us below.

We claim:

1. A reagent composition for coating onto needles of hypodermic syringes and needle containing medical devices contacting bodily fluids blood, mucous, saliva and semen, comprising:

a colorless, reduced leuco dye which upon contact with a bodily fluid containing a hydroperoxide catalyst will, upon oxidation, cause the coated needle to become visually colored, wherein the reduced leuco dye is selected from the group consisting of guaiac acid, Barfoeds solution, Benedicts solution, cresol, cathecol, phenylenediamine, Haynes solution, leuco malachite green, leucocrystal violet, peroxidase, pseudoperoxidase, tetramethylbenzedene and 2,2-azino-di-(3-ethylbenzyl)thiazoline sulfonic acid (ABTS).

2. A reagent composition for use on needles used in medical applications to test for blood, mucous, saliva, and semen comprising a solution of a hydroperoxide, wherein the hydroperoxide is cumene hydroperoxide, a chromogenic mixture of guaiac acid and 2,2-azino-di-(3-ethylbenzyl) thiazoline sulfonic and sodium sulfite, and a solvent comprising about 50% by volume of iron protoporphyrins, wherein the weight ratio of guaiac to 2,2-azino-di-(3-ethylbenzyl)thiazoline sulfonic acid in the chromogenic mixture is in the range of 1:6 to 6:1, and wherein the chromogen mixture is present in the solution in the range of 0.5 to 10% weight.

3. A needle for syringes and medical devices that come in contact with disease carrying fluids comprising:

a colorless needle which is coated with a reagent composition, wherein the reagent composition is a reduced leuco dye and wherein the reduced leuco dye is selected from the group consisting of guaiac acid, Barfoeds solution, Benedicts solution, cresol, cathecol, benenaphthol, phenylenediamine, Haynes solution, leuco malachite green, leuco-crystal violet, pyrogallol, peroxidase, o-phenylenediamine, 3-amino ethicarbazole, pseudoperoxidase, cumene hydroperoxide, tetramethylbenzedene and 2,2-azino-di-(3-ethylbenzyl)thiazoline sulfonic acid (ABTS) and which upon contact with a bodily fluid catalyst will, when oxidized, assume a visually detectable color.

* * * * *